United States Patent [19]
Fowler et al.

[11] Patent Number: 5,038,799
[45] Date of Patent: Aug. 13, 1991

[54] RESTRAINT SYSTEM

[76] Inventors: Neil E. Fowler; Shirley M. Fowler, both of P.O. Box 422, Dayton, Ohio 45405-0422

[21] Appl. No.: 456,388

[22] Filed: Dec. 26, 1989

[51] Int. Cl.⁵ .................................. A61F 13/00
[52] U.S. Cl. ..................... 128/878; 128/879
[58] Field of Search ............ 128/869, 870, 875, 876, 128/878, 882; 5/80, 443, 508; 248/214

[56] References Cited

U.S. PATENT DOCUMENTS

| | | | |
|---|---|---|---|
| 796,791 | 8/1905 | Anderson | 5/443 |
| 1,048,750 | 12/1912 | Smith | 5/443 |
| 1,172,103 | 2/1916 | Bennett | 128/876 |
| 2,332,035 | 10/1943 | Wickman | 128/876 |
| 3,297,026 | 1/1967 | Van Pelt | 128/892 |
| 4,046,143 | 9/1977 | Bell | 128/882 |
| 4,149,693 | 4/1979 | Lonigro | 248/214 |
| 4,628,925 | 12/1986 | Witzel | 128/882 |

FOREIGN PATENT DOCUMENTS 16658 of 1929 Australia ................. 5/508

Primary Examiner—Robert A. Hafer
Assistant Examiner—Charles H. Sam
Attorney, Agent, or Firm—Joseph Patrick Burke

[57] ABSTRACT

This disclosure is directed to a gentle, yet effective versatile restraint system for persons, e.g., patients, which permits exercise without impairment of circulation and can be readily fitted to beds, cribs, etc. to effectively restrain bed patients, children, senile and/or incontinent persons to prevent them from harming themselves and/or engaging in unhealthy practices. This restraint system contains a central tube or bar portion; mating end tube or bar portions; clamp means in conjunction with spring loaded pins to adjustably secure the end portions to side rails of a bed or crib; mounting rings slidably movable both inwardly and outwardly laterally along the central tube (bar) portion between a plurality of stops located so as to independently restrict the lateral movement of each mounting ring; soft, cushioned, strong, adjustable limb-restraining loop (cuff) members and connecting members connecting the mounting rings and the limb-restraining loop members to permit free, 360 degrees clockwise and counterclockwise, movement of the limb-restraining loop (cuff) members.

12 Claims, 2 Drawing Sheets

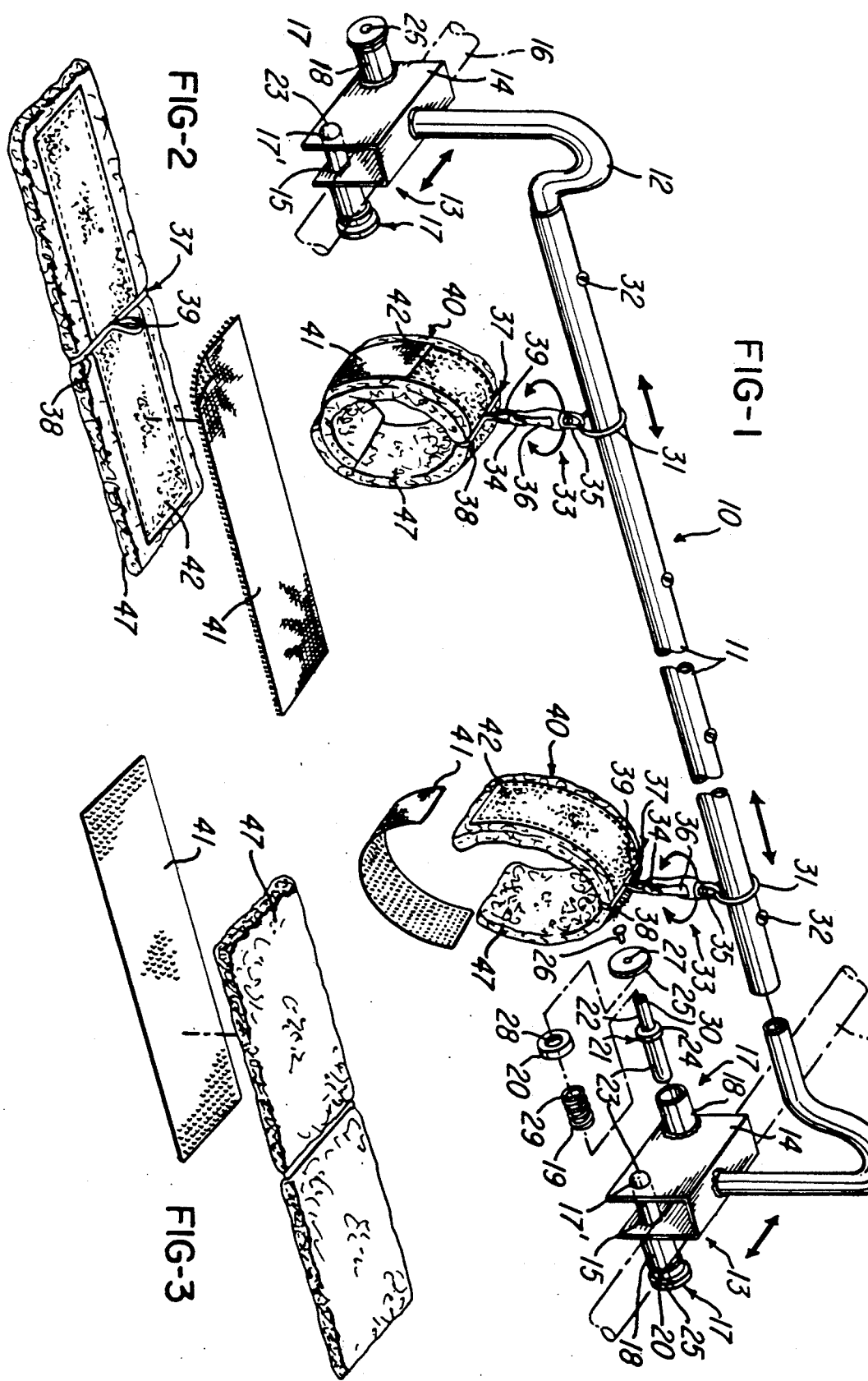

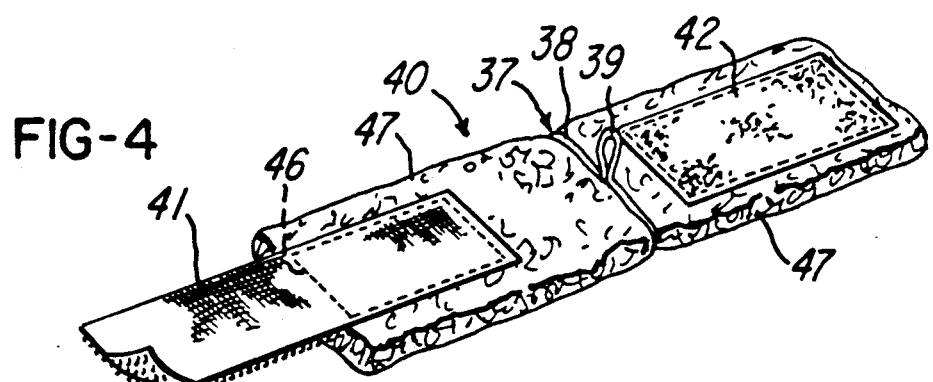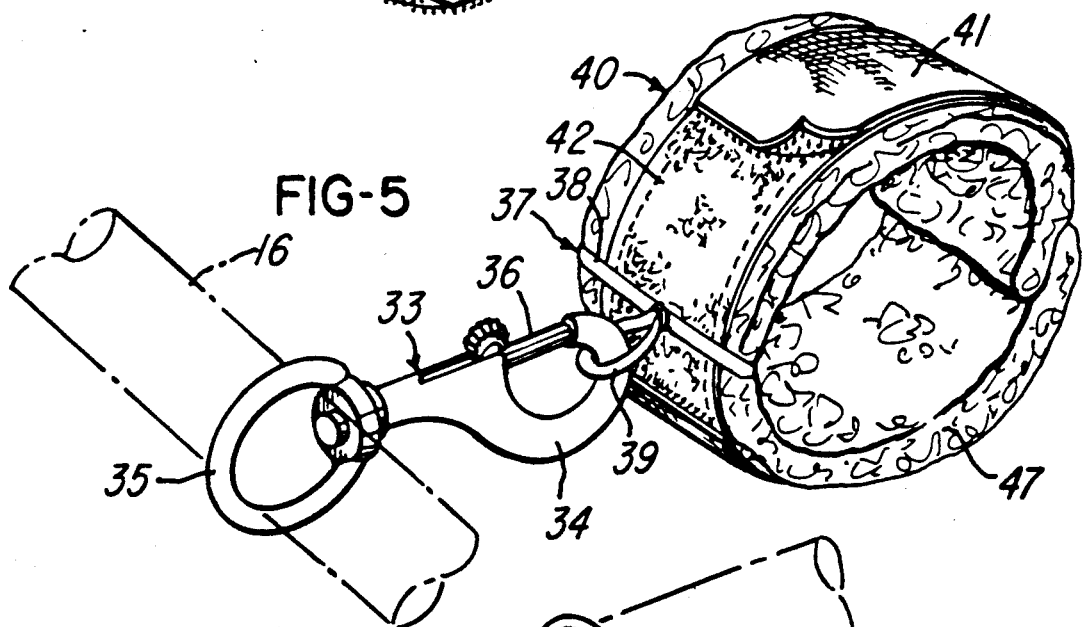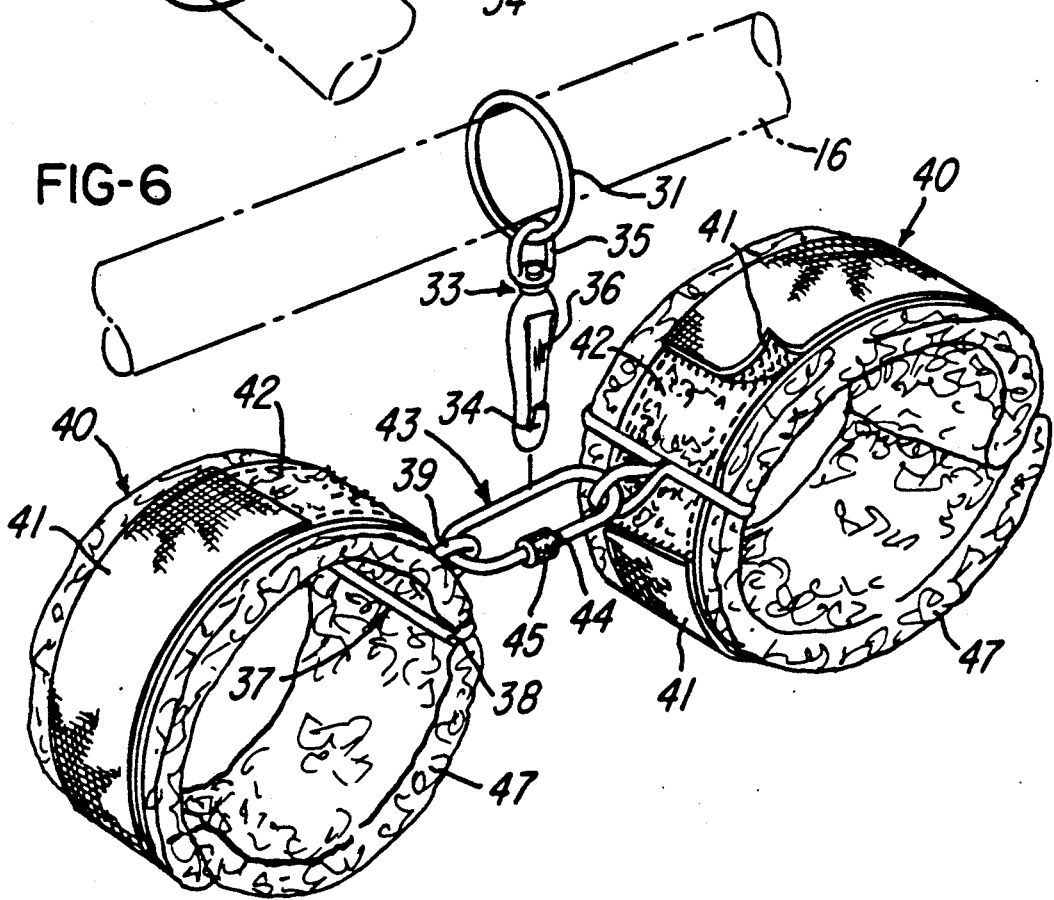

RESTRAINT SYSTEM

BRIEF DESCRIPTION OF THE INVENTION

The present invention is directed to a gentle, yet effective versatile restraint system for persons which permits exercise without impairment of circulation and can be readily fitted to beds, cribs, etc. to effectively restrain bed patients, children, senile and/or incontinent persons to prevent them from harming themselves and-/or engaging in unhealthy practices. This restraint system contains a central tube or bar portion; mating end tube or bar portions; means to adjustably secure the end portions to side rails of a bed or crib; mounting rings slidably movable both inwardly and outwardly laterally along the central tube (bar) portion between a plurality of stops located so as to independently restrict the lateral movement of each mounting ring; soft, cushioned, strong, adjustable limb-restraining loop (cuff) members and connecting members connecting the mounting rings and the limb-restraining loop members to permit free, 360 degrees clockwise and counterclockwise, movement of the adjustable limb-restraining loop (cuff) members.

BACKGROUND OF THE INVENTION AND PRIOR ART

Several problems exist in preventing various persons from engaging in unhealthy practices and/or preventing them from harming themselves while they are bedridden or present in a bed or crib of some type. For example, often the elderly have problems with senility and are incontinent individuals as well. Sometimes these problems are compounded by the fact that the incontinent individuals lack control over their bowels, so that they wet their bed and deposit feces in their environment where they sleep, eat, etc. Moreover such individuals can cause themselves to be infected by scratching various parts of their body, causing infection due to the presence of high concentrations of bacteria in the fecal and urine material present, e.g., under the fingernails.

Such people are not "dangerous" in the context of being criminals or seeking to inflict violent harm on others; but they are capable, if unrestrained, of injuring themselves. Such persons do not need the ultimate degree of restraint, as do dangerous criminals; but they do need to be restrained to prevent them from injuring themselves.

Since they are not dangerous to the general public, it is highly desirable to restrain them gently and effectively while at the same time avoiding impairing their circulation, which can be particularly critical in restraint of the elderly. Additionally, some form of restraint is often necessary to protect disoriented post-operative surgical patients from removing necessary equipment, e.g., intravenous tubing, catheters, etc., until such time as they have totally recovered from the anesthesia and/or painkillers employed to ease post-operative pain.

The desired objectives are to gently, yet effectively, restrain such patients or individuals in such a way as to avoid the unhealthy practices which may take place and which are referred to hereinabove while avoiding impairment of circulation.

The present invention accomplishes these seemingly contradictory objectives while permitting free movement of the patient's limbs in several directions, such as permitting them to rotate their respective bound limb(s), e.g., hands and wrists, and to exercise their restrained limbs in both inward and outward central lateral directions as well. The lateral central movement is restrained between stops located on the central bar portion of the restraining device whereas the rotational movement is unrestricted in accordance with one preferred embodiment of this invention.

Various attempts have been made in prior art devices to restrain the limbs and other body parts of patients. However, by and large, most of these devices involve total or near-total immobility of the party's limbs and other parts and will be discussed in more detail as follows.

U.S. Pat. No. 4,628,925, issued to Witzel, is directed to a quick-release limb holder apparatus for releasable affixation about a patient's limb to secure the patient, as desired, to an affixed object, such as a hospital bed, in order to immobilize the patient. An adjustable and independently separable series of straps encircles the patient's limb in a manner which permits the patient to be quickly freed from a restrained position within the apparatus without necessitating the complete disassembly of adjustment straps as well as obviating the need for readjustment of the straps upon reaffixation of the apparatus about the patient's limb. A cuff is interposed between the encircling straps and the patient's skin to cushion and insulate the patient's limb from forces exerted by the encircling straps to attempt to thereby minimize any potential for abrasion, irritation or other discomfort.

However, it will be observed that when pressure is applied upon exertion of movement past a given position upon the patient's restrained limb(s), directly by the series of straps, buckles and swivels, much like a choker chain on an animal; viz., the more force that is exerted by the restrained person to move this limb(s), the greater will be the compressing pressure exerted by the Witzel buckles and swivels. Such pressure is likely to impinge on nerves and blood vessels impairing circulation and resulting in pain and bruises, which is contrary to the objectives of the present invention, viz., to permit the restrained party to obtain exercise by movement both centrally laterally and rotationally without in any way increasing the compressive pressure exerted by the restraint. Thus it will be observed that in the structure of the restraint system of this invention, none of the metal work encircles the restraining loop(s) or cuff(s), which is not true in the restraint of Witzel.

U.S. Pat. No. 3,474,781, issued to Gaylord, Jr., is directed to a restraining device for bedridden persons, which restraining device prevents lateral movement of the limbs and other encircled body parts but severely restricts rotational movement thereof at the point of restraint. The Gaylord, Jr. restraint device fails to enable the patient or other restrained individual to have the benefits of movement in several separate directions between stops and could very well exert undesirable pressure on the limbs resulting in bed sores and abrasions.

U.S. Pat. No. 4,046,143, issued to Bell, is directed to a restraint device having a bar separating two leg cuffs. which would prevent heart patients from crossing their legs, which permits freer blood circulation. The Bell device, of course, fails to enable the patient to have independent lateral movement of each restrained limb and prevents rotational movement thereof at the point of restraint. When the cuffs (12) and (14) are made of metal, pressure exerted there against by the restrained ankle of the patient will produce pressure with its consequent deprivation of circulation to the patient at the point of restraint. This is undesirable and does not occur with the use of the device of this invention.

U.S. Pat. No. 3,535,718, issued to Murcott, is directed to the use of limb restraint devices at the vicinity of the patient's wrists and ankles, which restraints prohibit the inward lateral movement of the upper restrained limbs and apparently prevent upward and both inward and outward lateral movement of the lower limbs, as shown in FIG. 1 of Murcott. Moreover, since the rigid metal loops (14) are part of the structure which encircles the restrained limbs, exertion of force there against by the wearer will necessarily produce unyielding pressure in the vicinity of the restraint strap. The Murcott restraint device thereby prohibits lateral exercise of the arms by the patient so restrained in an inward manner and prevents both lateral inward and outward movement of the legs, which undoubtedly would cause a detrimental effect upon the sense of well being of the restrained individual. Applicant's restraint system, on the other hand, permits lateral movement in both directions, viz., inwardly and outwardly with respect to both restrained limbs as well as permitting free rotational movement thereof both clockwise and counterclockwise.

U.S. Pat. No. 3,297,026, issued to Van Pelt, is directed to a restraining device for restraining the limbs of a patient by securing its encircling strap(s) directly to a fixed object(s), such as a stationary rod, such as a bed. When such Van Pelt restraints are tethered directly to bed side rails, e.g., exercising movement in both inward and outward directions in the central portion of the bed would not be available to the restrained anatomical body. As will be noted from FIG. 1 of Van Pelt, the Van Pelt restraining device fails to permit the central lateral inward and outward movement of the restrained limb within stops. This movement is permitted by the present invention.

U.S. Pat. No. 4,414,969, issued to Heyman, is directed to a restraint device wherein a strap and ring arrangement encircles the limb of the wearer at the point where the restraint is imposed. Consequently tightening of the encircling member can occur within certain limits when the patient pulls or otherwise exerts pressure in a direction of movement away from the support where the other end of the strap is affixed. Moreover, the wrist restraint of Heyman suffers from the same shortcomings as those discussed above in regard to Van Pelt and prevents lateral inward movement of the wearer's limbs. The Heyman restraint fails to accomplish the objectives of this invention which include central movement of the restrained limbs laterally both inwardly and outwardly.

U.S. Des. Pat. No. 254,214, issued to Leary, is directed to an ornamental design for a limb and/or body restraint, as shown and described in FIGS. 1, 2 and 3. This design patent fails to disclose the structure of the restraint system of the present invention.

U.S. Pat. No. 3,942,525, issued to Dragan, is directed to an athletic wrap adapted to encircle a portion of the body of the wearer, e.g., the elbow joint, to lessen the likelihood of an athlete exerting sufficient strain or stress on the wrapped body part to create a debilitating condition such as "tennis elbow". Dragan fails to disclose the present invention.

BRIEF DESCRIPTION OF THE DRAWINGS

FIG. 1 is an isometric view with parts exploded illustrating the environment of use of the restraining device of this invention when attached, e.g., to either upper or lower bed side rails.

FIG. 2 is an isometric view of a soft, cushioned, strong, adjustable limb-restraining member forming a component of the restraint system of this invention.

FIG. 3 is an isometric view illustrating the soft, strong, porous cushion layer and its positional arrangement prior to assembling it with the upper binder material layer used in accordance with this invention for adjustably determining the inner diameter of the limb-restraining member of FIG. 2.

FIG. 4 is a perspective view illustrating the limb restraining member as in FIG. 1 assembled with its upper binder material layer positioned in place by attachment and ready for use in accomplishing the adjustable determination of the inner diameter of the limb-restraining member.

FIG. 5 is a perspective view of a limb-restraining member as shown in FIG. 4 wherein a soft, cushioned, strong, adjustable, limb-restraining member is connected to the overhead central tube (bar) portion by a securing means.

FIG. 6 illustrates an embodiment of this invention which is an alternative to that illustrated in FIG. 5, with FIG. 6 showing a pair of soft, cushioned, strong, adjustable limb-restraining members whose patient binder loops are attached to one another via a closed loop link joining said limb-restraining members via binder loops positioned on each such restraining member so that when the patient's limb exerts lateral pressure, the pressure is exerted in a direction perpendicular to the long axis of the restrained limb.

DETAILED DESCRIPTION OF THE INVENTION

As will be apparent from FIG. 1, the restraint system 10 of this invention has a central overhead tube (or bar) portion 11 which is joined to a pair of mating and overhead end tubes (or bar) portions 12. The end tube (or bar) portions 12 can be of smaller outer diameter than the inner diameter of the central tube or bar portion 11, or vice versa.

Securing means 13 to adjustably secure the end tube portions 12 to the bed side rails 16 can comprise substantially U-shaped clamp members 14 having one or more and preferably a plurality of circular openings 15 on the inboard and outboard sides thereof to permit use of quick release, constant tension spring pins 17 to adjustably secure means 13 to rails 16. Alternatively, but less preferably, carriage bolts in conjunction with washers, which may be lock washers, and nuts, e.g., wing nuts, can be used to secure adjustably the clamp means 13 to the bed or crib side rails. A plurality, e.g., two, of these constant tension spring pins 17 or equivalent adjustable, quick release securing means can be used on each clamp means 13 to firmly secure the end overhead tubes 12 to the bed or crib side rails 16. As is shown on the left and right sides of FIG. 1, each distal portion 23 of quick release securing means 17 passes through an opening 17' on the inner side of each securing means 13.

As will be apparent from FIG. 1, each adjustable quick release securing means 17 has a spring chamber 18 containing a constant tension coil spring 19 and cap 20 through which there is inserted pin 21 having reduced diameter distal portion 23, inner proximal portion 22 and medial portion shoulder stop 24. Head 25 serves to compress the coil spring at a constant tension when rivet 26 is passed through the smaller opening 27 of head 25, the larger opening 28 of cap 20, the central passageway 29 of spring 19 and into the mating opening 30 of distal pin portion 23 to complete the quick release pin assembly.

Mounting means 31 can take the form of rings having a larger inner diameter than the outer diameter of the central tube portion so that they slide along central overhead tube 11 between stops 32. The stops 32 can, e.g., be screws or static rings having an outer diameter larger than the inner diameter of rings 31 welded or adhered to central overhead tube 11 at the desired locations. Moreover, since the stops are located on the central bar portion, the limbs can be moved laterally closer to the center of the patient's body which is not the case when restraining cuff(s) are tethered directly to bed side rails.

Securing means 33, e.g., snap swivels, preferably spring-loaded snap swivels, each have a hook portion 34, an eye portion 35 and a catch portion 36. The hook portion of each snap swivel is connected to a small loop 37 stitched or otherwise fixedly attached, e.g., glued, at 38 to form the fixed loop portion shown at 39. Fixed loop 37 is thus attached to soft, cushioned, strong, adjustable loop limb-restraining members 40 of which there are a pair shown in the restraint system of FIG. 1.

It should be noted that a plurality of such restraints, e.g., four, can be utilized in the event that it is desirable or necessary to gently restrain the arms and legs of a patient with one pair of adjustable loop restraining members 40 being used for the ankles and the other pair being used at the wrists of the wearer. By placing the restraint system mounting means on the middle or lower bed side rails, this permits the wearer to lie on his/her back while resting his/her hands on the upper body area. Alternatively, by placing the wearer lying on either side and snapping both left and right limb adjustable restraining members 40 of both hands on a single eye swivel (FIG. 6), the wearer may still roll over onto his/her back to give more freedom of movement, e.g., while sleeping.

Moreover, it is within the purview of this invention to use a plurality of limb-restraining members at different locations on the same limo, e.g., on the wearer's upper thigh and ankle on one side of a wearer.

Similarly, one limb-restraining member can be used at the wearer's wrist and another on the upper calf on the same side of the wearer's body, thus allowing removal of pressure from certain areas of the wearer's back in cases of patients who are habitually bedridden. These various, uses of the present restraint system highlight its versatility.

These adjustable limb-restraining members 40 are comprised of a soft, strong, porous cushion layer, for example, that material commercially available under the trade name "VELLUX".

Upper binder material layer 41, for adjustably determining the inner diameter of limb-restraining member 40, and coacting, mating lower binder material layer 42 can be, and preferably are, the commercially available material marketed under the trademark of "Velcro". One layer of this binding material can be the one containing the so-called "pile" and the other layer can be the one containing the "loops" or "hooks".

According to an alternative embodiment of this invention, in the event that it s necessary or desirable to restrain both upper or lower limbs of a patient in a side-by-side manner, a closed loop link 43, one end portion of which is externally threaded at 44, can be employed as shown in FIG. 6 to accomplish this. It will be observed that rotatable locking sleeve 45 having internal threads mating with the external threads of the loop end portion 44 of loop end 43 can be used then to join the fixed small loop portions 39 of adjustable patient binder loops 40. In this case the hook portion 34 of the securing means 33 is attached to the closed loop link 43 rather than to fixed loop portion 39 of securing means 33. FIG. 4 illustrates the use of sewn stitches 46 as attachment means to attach upper binder material layer 41 to porous cushion cuff layer 47. This attachment means 46 can be permanent or temporary.

FIGS. 2 and 3 show Velcro binder material 41 not attached or sewn to the Vellux cuff 47 in order to give maximum flexibility of sizing for wrists or leg restraints.

FIG. 4 shows Velcro binder 41 permanently attached to the Velux cuff 47 as a matter of convenience and to prevent loss when laundering.

We claim:

1. A gentle, yet effective, versatile restraint system for persons which permits exercise without impairment of circulation comprising a central tube (bar) portion; mating end tube (bar) portions; means located on the end tube (bar) portions to adjustably secure said end tube (bar) portions to side rails of a bed (crib); mounting rings slidably movable laterally along the central tube (bar) portion; a plurality of stops on said central tube (bar) portion located so as to independently restrict the lateral movement of each mounting ring; soft, cushioned, strong, adjustable limb-restraining loop members and connecting members connecting said mounting rings and said limb-restraining loop members to permit free clockwise and counter-clockwise movement of said limb-restraining loop members.

2. A restraint system as in claim 1 wherein said connecting members are snap swivels.

3. A restraint system as ian claim 2 wherein said limb-restraining loop members have co-acting mating pile and loop (hook) layer portions attached thereto.

4. A restraint system as in claim 3 wherein said co-acting mating portions are attached to said limb-restraining loop members by stitches.

5. A restraint system as in claim 4 wherein each limb restraining loop member contains a small loop portion fixedly attached thereto.

6. A gentle, yet effective, versatile restraint system for persons which permits exercise without impairment of circulation comprising a central tube (bar) portion; mating end tube (bar) portions; clamps and quick release constant tension spring pins inserted through openings in said clamps located on the end tube (bar) portions to adjustably secure said end tube (bar) portions to side rails of a bed (crib); mounting rings slidably moveable laterally along the central tube (bar) portion; a plurality of stops on said central tube (bar) portion located so as to independently restrict the lateral movement of each mounting ring; soft, cushioned, strong, adjustable limb-restraining loop members each having coacting mating binder layers secured thereto and snap swivels connecting said mounting rings and said limb-restraining loop members to permit free clockwise and counter-clockwise movement of said limb-restraining loop members.

7. A gentle, yet effective, versatile restraint system for persons which permits exercise without impairment of circulation comprising a central tube (bar) portion; mating end tube (bar) portions; substantially U-shaped clamp members, each having a plurality of openings on the inboard and outboard sides thereof and a plurality of quick release constant tension spring pins inserted through said openings to adjustably secure said end tube (bar) portions to side rails of a bed (crib); mounting rings slidably movable laterally along said central tube (bar) portion; a plurality of stops on said central tube (bar) portion located so as to independently restrict the lateral movement of each mounting ring; adjustable limb-restraining loop members each having coacting mating pile and loop (hook) layers secured thereto and each having small loop portions fixedly attached thereto; and snap swivels connecting each small loop of said adjustable, limb-restraining loop member to each of said mounting rings.

8. A restraint system as in claim 7 wherein said small loop portions are fixedly attached to said limb-restraining loop members by stitches.

9. A restraint system as in claim 8 wherein said small loop portions are fixedly attached to said limb-restraining loop members by glue.

10. A gentle, yet effective, versatile restraint system for persons which permits exercise without impairment of circulation comprising a central tube (bar) portion; mating end tube (bar) portions; means located on the end tube (bar) portions to adjustably secure said end tube (bar) portions to side rails of a bed (crib); mounting rings slidable movable laterally along the central tube (bar) portion; a plurality of stops on said central tube (bar) portion located so as to independently restrict the lateral movement of each mounting ring; a pair of soft, cushioned, strong, adjustable limb-restraining loop members each having a small loop portion; a closed loop link connecting said pair of limb-restraining loop members via said small loop portion; and a snap swivel connecting one of said mounting rings to said closed loop link.

11. A restraint system as in claim 10 wherein said adjustable limb-restraining loop members have coacting mating pile and loop (hook) layer portions attached thereto.

12. A restraint system as in claim 11 wherein said coacting mating layer portions are secured to said limb-restraining loop members by stitches.

* * * * *